United States Patent [19]

Okimatsu et al.

[11] Patent Number: 5,437,834
[45] Date of Patent: Aug. 1, 1995

[54] POROUS LIVING BODY REPAIRING MEMBER, AND A METHOD OF IMPARTING ELASTICITY TO IT

[75] Inventors: Hideaki Okimatsu; Yasunori Tamura, both of Gamou, Japan

[73] Assignee: Kyocera Corporation, Kyoto, Japan

[21] Appl. No.: 133,655

[22] Filed: Oct. 7, 1993

[30] Foreign Application Priority Data

Oct. 8, 1992 [JP] Japan .................. 4-270371

[51] Int. Cl.$^6$ .............................................. B22F 3/16
[52] U.S. Cl. ........................................ 419/24; 419/5; 419/23; 419/28; 419/38; 419/56; 419/60
[58] Field of Search .................. 419/5, 23, 24, 28, 38, 419/56, 60; 228/193

[56] References Cited

U.S. PATENT DOCUMENTS 4,636,219  1/1987  Pratt et al. ..................... 623/22
4,693,721  9/1987  Ducheyne ..................... 623/16

FOREIGN PATENT DOCUMENTS 0225838  6/1987  European Pat. Off. .
0366018  5/1990  European Pat. Off. .
0526682  2/1993  European Pat. Off. .

Primary Examiner—Donald P. Walsh
Assistant Examiner—John N. Greaves
Attorney, Agent, or Firm—Spensley Horn Jubas & Lubitz

[57] ABSTRACT

A porous living body repairing member obtained by compression-molding a metal fiber material into a desired shape, sintering the fiber mesh body or thereafter, and imparting a compressive stress of not more than 4.00 to 40.0 MPa to provide a porous living body repairing member having a compressive elasticity of not more than 2000 MPa and a permanent deformation of not more than 1% under a stress below a compressive yield stress.

The compressive yield stress becomes approximately equal to the above compressive stress, and almost complete elasticity of a permanent deformation rate of not more than 0.1% is shown with respect to a compressive stress below this compressive yield stress. Accordingly, even when the porous living body repairing member is used at a high compressive load site such as man's lumbar body, permanent deformation hardly occurs. Since the member of this invention has a compressive elasticity of not more than 2000 MPa, when it is transplanted within the living body, its stress to the bone is well transmitted, and it acts advantageously to the bone ingrowth in the pore. At the same time, bone absorption around the repairing member is not developed which may occur by the shielding off of the stress as is seen in a living body repairing member having a high elasticity.

1 Claim, 1 Drawing Sheet

POROUS LIVING BODY REPAIRING MEMBER, AND A METHOD OF IMPARTING ELASTICITY TO IT

DETAILED DESCRIPTION OF THE INVENTION

1. Field of the Invention

The present invention relates to a porous living body repairing member used in a medical treatment field, for example, orthopedic surgery, neurological surgery, oral surgery, and dental, and a method of treatment for imparting elasticity thereto.

2. Prior Art

As a porous living body repairing member having a compressive elasticity close to a bone, there has been a porous living body repairing member produced by compression-molding a metallic fiber material (first compressing a metallic fiber material and accumulating it), and thereafter sintering it in vacuo as shown in the porous repairing member described in Japanese Laid-Open Patent No. 109867/1988. Such a porous living body repairing member has an elasticity close to a bone, and after a certain period of time, the surface of the bone and an inner growth of the bone in the surface of the porous body immediately adjoining the bone produce a biological fixation. When it was transplanted with a bone cementing agent such as a bone cement made of polymethyl methacrylate, the intrusion of this bone cementing agent in the porous material can give a mechanical fixation with the bone.

Such a porous living body repairing member shows an improvement over the conventional living body repairing members in respect of compressive elasticity and strength. But when it is used in a highly compressive load site such as the spine and a hip joint in the living body, strain after removing a compressive stress is developed, namely permanent plastic deformation is developed.

The above-mentioned porous living body repairing member, as is generally believed, does not show elasticity under compressive load below the compressive yield stress, but actually shows a behavior near viscoelasticity. When a compressive stress above a certain limit is imparted and then eliminated, strain remains.

When the porous living body repairing member is transplanted into the living body and thereafter this deformation occurs, the biological fixation by the bones ingrowth into the porous bodies is disintegrated, with the result that "loosenings" of the living body repairing member are developed, and serious problems such as the dropping of the porous living body repairing member arise.

It is an object of this invention to provide a porous living body repairing member having almost complete elasticity under a load below the compressive yield stress in order to prevent the occurrence of permanent deformation while maintaining a compressive elasticity near a bone to solve the above problem of the conventional technique and a method of treatment for imparting almost complete elasticity.

To solve the above problem, a metallic fiber material is compression-molded to a desired form in the present invention and a compressive stress is imparted to the shaped body to make a porous living body repairing member. The compressive yield stress of the porous living body repairing member so treated is approximately equal to the above compressive stress. Furthermore, with respect to a compressive stress of not more than the compressive yield stress, an approximately complete elasticity of a permanent deformation rate of not more than 0.1% will be shown. Accordingly, when the porous living body repairing member is used at a high compressive load site of, for example, man's lumbar body, permanent deformation is hardly developed. Further, the magnitude of the said compressive stress may be below the maximum compressive stress which the porous repairing member of the present invention receives. When the above compressive stress is smaller, the compressive elasticity becomes smaller.

When the porous living body repairing member is adjusted to a compressive stress of not more than 40.0 MPa, its compressive elasticity can be adjusted to not more than 2100 MPa. However, when the compressive stress is lower than 4.0 MPa, its compressive yield stress becomes too small. Accordingly, then the porous living body repairing member does not become serviceable at any site in the living body.

For example, as compared with an elasticity of titanium alone or an alumina ceramic which is 110000 MPa or 390000 MPa, the porous living body repairing member of the invention has a compressive elasticity of as low as not more than 2100 MPa. It is relatively near a compressive elasticity of cancellous bone of man which is 60 to 130 MPa. When it is transplanted within the living body, stress of the bone is well transmitted. It acts advantageously for the bone ingrowth to the porous body. As seen in the living body repairing member having a high compressive elasticity, bone absorption around the living body repairing member is not developed as brought about by the shielding off of the stress.

EXAMPLES

Examples of the invention will be illustrated by using the drawings.

EXAMPLE 1

Figure 1:
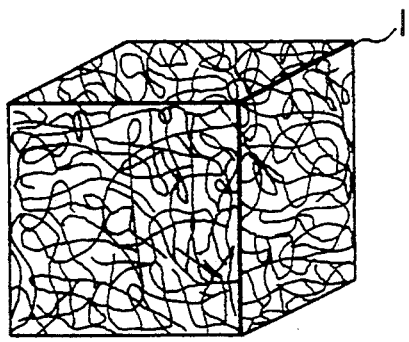
FIG. 1 is a perspective view of the fiber mesh body illustrated in Example 1.

A titanium fiber material having a fiber diameter of 250 μm was knitted into a net. It was rounded and filled in a metal mold with a 15×15 mm square section, and press-molded at a pressure of about 150 MPa. It was sintered in vacuo at about 1300° C. to obtain an fiber mesh body having a cubic shape with a porosity of about 50% as shown in FIG. 1.

A compressive stress of 20 MPa and 40 MPa was imparted to fiber mesh bodies to obtain test bodies constituting porous living body repairing members.

Using these test bodies, permanent deformation rates were measured. Furthermore, compressive elasticies of these test bodies were measured. The results are shown in Table 1.

TABLE 1

|  | Permanent deformation rate (%) | Compressive elasticity(MPa) |
| --- | --- | --- |
| Comparative Example | 0.85 | 1473 |
| Example 1 (20 MPa) | 0.02 | 1874 |
| Example 1 | 0.02 | 2051 |

TABLE 1-continued

| | Permanent deformation rate (%) | Compressive elasticity(MPa) |
|---|---|---|
| (40 MPa) | | |

As Comparative Example, the cubic fiber mesh body was produced. After sintering in vacuo, the above compressive stress was not applied to form a test body of Comparative Example. The compressive elasticity of this test body was measured and shown in Table 1.

As is clear from Table 1, the test body of Comparative Example had a permanent deformation rate of approximately 1%, but the test bodies according to the present invention had a permanent deformation rate of not more than 0.1% and a compressive elasticity of 2100 MPa or below.

EXAMPLE 2

Figure 2:
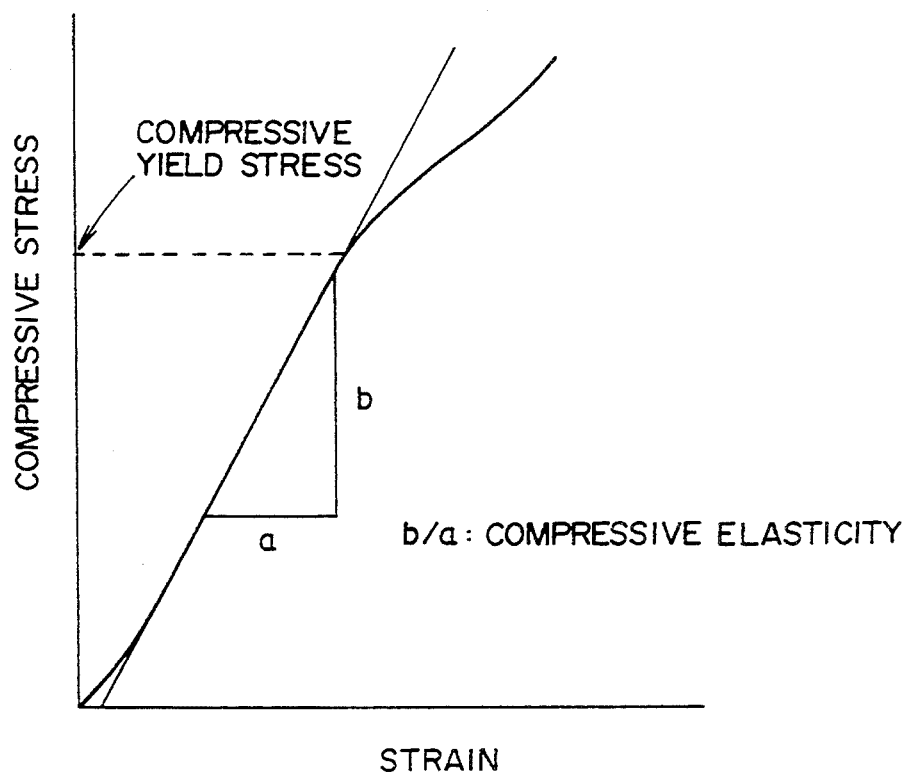
FIG. 2 is a graphic representation showing the relation between compression stress and strain.

Fiber mesh bodies 1 were produced by the method of Example 1. Compressive stresses shown in Table 2 were applied in a perpendicular direction to the mold pressurizing direction to produce test bodies, and such stresses were so applied to the produced test bodies. (a) Compressive yield stress, (b) compressive elasticity under a compressive stress of not more than the above compressive yield stress and (C) permanent deformation rate (see FIG. 2) after removal of the load of each test body were measured. The results are shown in Table 2.

TABLE 2

| Compressive stress Kgf (MPa) | Compressive yield stress/MPa | Compressive elasticity/ MPa | Permanent deformation rate (%) |
|---|---|---|---|
| 100 (4.00) | — | 1256 | 0.03 |
| 200 (9.00) | 6.00 | 1617 | 0.03 |
| 300 (13.00) | 10.00 | 1752 | 0.04 |
| 400 (18.00) | 14.00 | 1858 | 0.02 |
| 500 (22.00) | 17.00 | 1825 | 0.02 |
| 600 (27.00) | 21.00 | 1918 | 0.00 |
| 700 (31.00) | 26.00 | 1910 | 0.02 |
| 800 (35.00) | 30.00 | 1970 | 0.04 |
| 900 (49.00) | 33.00 | 1972 | 0.01 |
| 1000 (44.00) | 37.00 | 1953 | 0.09 |

As is clear from Table 2, the compressive yield stress is approximately equal to the compressive stress given to the fiber mesh body 1. Furthermore, after removing the load, the permanent deformation rate becomes not more than 1%. If a compressive stress is imparted in a range of up to 40 MPa, it is possible to maintain the compressive elasticity at not more than 2100 MPa. Furthermore, when stepwise compressive loads are applied in the same direction as the mold pressurizing direction, the similar results can be obtained.

The compressive stress may be applied simultaneously in the step of sintering in vacuo, but the apparatus becomes large-sized and involves a problem of facilities.

In the present invention, a metal fiber material is compression-molded into a desired shape, and compressive stress is imparted to the resulting fiber mesh body to obtain a porous living body repairing member. The compressive yield stress of the porous repairing member subjected to such a treatment is approximately equal to the above compressive stress. Approximately complete elasticity having a permanent deformation rate of not more than 0.1% is shown against compressive stress below this compressive yield stress. Accordingly, even when the repairing member is used at a high compressive load site such as man's lumber body, permanent deformation hardly occurs. Furthermore, by adjusting the compressive stress to not more than 40 MPa, it is possible to adjust the compressive elasticity to not more than 2000 MPa. When the repairing member is transplanted within the living body, the stress to the bone is well transmitted. It acts advantageously to the bone ingrowth within the pore, and at the same time, bone absorption around the repairing member which is brought about by the shielding off of the stress is not developed, as is seen in the living body repairing material having a high elasticity.

Since the above-mentioned effect can be achieved by a simple method of imparting compressive stress, the product of the invention is clinically very effective as a living body repairing member, and contributes greatly to human welfare.

What is claimed is:

1. A method for imparting elasticity to a porous living body repairing member, comprising:
    compression-molding a metal fiber material into a fiber mesh body having a compressive elasticity and a desired shape,
    sintering the resulting fiber mesh body in vacuo,
    imparting a compressive stress of between 4.00 and 40.0 MPa to the fiber mesh body using a compressive load, and
    adjusting the compressive elasticity of the fiber mesh body to an amount not greater than 2000 MPa,
    whereby the fiber mesh body exhibits a permanent deformation rate of not more than 0.1% under a stress below a compressive yield stress substantially equal to the compressive stress.

* * * * *